United States Patent
Taftaf et al.

(10) Patent No.: US 9,663,596 B2
(45) Date of Patent: May 30, 2017

(54) CATALYST COMPOSITION FOR POLYMERIZATION OF OLEFINS

(71) Applicant: Saudi Basic Industries Corporation, Riyadh (SA)

(72) Inventors: Mansour Taftaf, Peninsula, OH (US); Jaiprakash Brijlal Sainani, Gujarat (IN); Vladimir Aleksandrovich Zakharov, Geleen (NL); Gennadii Dimitrievich Bukatov, Geleen (NL); Vimalkumar Mahendrabhai Patel, Gujarat (IN); Sergei Andreevich Sergeev, Geleen (NL); Martin Alexander Zuideveld, Kelmis (BE); Aurora Alexandra Batinas-Geurts, Sittard (NL)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 48 days.

(21) Appl. No.: 14/762,279

(22) PCT Filed: Jan. 28, 2014

(86) PCT No.: PCT/EP2014/051609
§ 371 (c)(1),
(2) Date: Jul. 21, 2015

(87) PCT Pub. No.: WO2014/118164
PCT Pub. Date: Aug. 7, 2014

(65) Prior Publication Data
US 2015/0353656 A1 Dec. 10, 2015

Related U.S. Application Data

(60) Provisional application No. 61/927,029, filed on Jan. 14, 2014, provisional application No. 61/927,034, filed on Jan. 14, 2014.

(30) Foreign Application Priority Data

Jan. 31, 2013 (EP) ..................... 13000481
Jan. 31, 2013 (EP) ..................... 13000492
Dec. 20, 2013 (EP) ..................... 13199147
Dec. 20, 2013 (EP) ..................... 13199160

(51) Int. Cl.
| | |
|---|---|
| C08F 110/06 | (2006.01) |
| C07C 233/23 | (2006.01) |
| C07C 233/18 | (2006.01) |
| C07C 233/69 | (2006.01) |
| C08F 4/655 | (2006.01) |
| C08F 4/649 | (2006.01) |

(Continued)

(52) U.S. Cl.
CPC .......... *C08F 110/06* (2013.01); *C07C 233/18* (2013.01); *C07C 233/23* (2013.01); *C07C 233/69* (2013.01); *C08F 4/649* (2013.01); *C08F 4/655* (2013.01); *C08F 4/6546* (2013.01); *C08F 10/06* (2013.01); *C07C 2101/14* (2013.01)

(58) Field of Classification Search
None
See application file for complete search history.

(56) References Cited

U.S. PATENT DOCUMENTS 6,395,670 B1    5/2002   Morini et al.

FOREIGN PATENT DOCUMENTS

| EP | 0398698 B1 | 12/1995 |
|---|---|---|
| EP | 1222214 B1 | 7/2004 |

(Continued)

OTHER PUBLICATIONS

International Search Report and Written Opinion for PCT/EP2014/051609 mailed Apr. 24, 2014, 11 pages.

(Continued)

*Primary Examiner* — Catherine S Branch
(74) *Attorney, Agent, or Firm* — Cantor Colburn LLP

(57) ABSTRACT

A catalyst composition comprising a monoester, the compound represented by formula (I) as an internal electron donor, and optionally an additional internal electron donor selected from a group consisting of diesters and diethers,

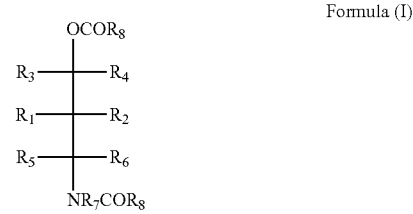

Formula (I)

wherein: $R_1$, $R_2$, $R_3$, $R_4$, $R_5$ and $R_6$ are hydrogen, straight, branched and cyclic alkyl having at most 20 carbon atoms and aromatic substituted and unsubstituted hydrocarbyl having 6 to 20 carbon atoms, $R_7$ is a straight, branched and cyclic alkyl having at most 20 carbon atoms and aromatic substituted and unsubstituted hydrocarbyl having 6 to 20 carbon atoms, and $R_8$ is an aromatic substituted and unsubstituted hydrocarbyl having 6 to 20 carbon atoms. Also described is a process for preparing the polymerization catalyst composition, a polymerization catalyst system comprising the catalyst composition, a co-catalyst and optionally an external electron donor; and use of the catalyst system for polymerization of olefins.

18 Claims, No Drawings

(51) Int. Cl.
*C08F 4/654* (2006.01)
*C08F 10/06* (2006.01)

(56) References Cited

FOREIGN PATENT DOCUMENTS

| | | |
|---|---|---|
| EP | 1838741 B1 | 4/2011 |
| EP | 2027164 B1 | 8/2012 |
| WO | 9632426 A1 | 10/1996 |
| WO | 9957160 A1 | 11/1999 |
| WO | 02100904 A1 | 12/2002 |
| WO | 2004054711 A1 | 7/2004 |
| WO | 2007134851 A1 | 11/2007 |
| WO | 2011106497 A1 | 9/2011 |
| WO | 2012017040 A1 | 2/2012 |
| WO | 2014118165 A1 | 8/2014 |
| WO | 2006056338 A1 | 6/2015 |

OTHER PUBLICATIONS

Vaughan, Wyman, et al., "Synthesis of Potential Anticancer Agents, V. Azetidines", Journal of Organic Chemistry. vol. 26, Jan. 1, 1961, pp. 138-144.

Pullukat, Thomas J. and Hoff, Raymond E., "Silica-Based Ziegler-Natta Catalysts: A Patent Review", Catal. Rev.—Sci. Eng., vol. 41 (3 & 4), 389-428 (1999).

CATALYST COMPOSITION FOR POLYMERIZATION OF OLEFINS

This application is a national stage application PCT/EP2014/051609, filed Jan. 28, 2014, which claims priority to U.S. Provisional Application Ser. No. 61/927,029 filed Jan. 14, 2014, U.S. Provisional Application Ser. No. 61/927,034 filed Jan. 14, 2014, European Patent Application 13000481.5 filed Jan. 31, 2013, European Patent Application 13000492.2 filed Jan. 31, 2013, European Patent Application 13199147.3 filed Dec. 20, 2013, and European Patent Application 13199160.6 filed Dec. 20, 2013, which are hereby incorporated by reference in their entirety.

The invention relates to a catalyst composition for polymerization of olefins. The invention also relates to a process for preparing said catalyst composition and to a catalyst composition obtained by this process. Furthermore, the invention is directed to a catalyst system for polymerization of olefins comprising the said catalyst composition, a co-catalyst and optionally an external electron donor; and to a process of making polyolefins by contacting an olefin with said catalyst system. The invention also relates to the use of said catalyst composition in the polymerization of olefins.

Ziegler-Natta catalyst systems and their components are commonly known as being suitable for preparing polyolefins, such as for example polypropylene. The term is known in the art and it typically refers to catalyst systems comprising a transition metal containing solid catalyst compound; an organo-metal compound and optionally one or more electron donor compounds (external donors). The transition metal containing solid catalyst compound comprises a transition metal halide, i.e. titanium, chromium, vanadium halide supported on a metal or metalloid compound, such as magnesium chloride or silica. An overview of such catalyst types is for example given by T. Pullukat and R. Hoff in Catal. Rev.-Sci. Eng. 41, vol. 3 and 4, 389-438, 1999. It is generally known that for instance by varying the transition metal; the type of support; the internal/external donors; the co-catalyst type; by adding additional compounds; and/or by introducing certain components in different process steps of making Ziegler-Natta types of catalysts, the catalyst activity, morphology and the properties of the polyolefins made by using such catalysts, such as isotacticity can be tuned. For instance, document WO96/32426A discloses a 3-step process for producing a catalyst for the polymerization of an olefin, wherein in the first two steps a compound $Mg(OAlk)_xCl_y$ of certain morphology is prepared, and subsequently this solid Mg-compound is contacted with titanium tetrachloride, and an internal electron-donating compound, which is dibutyl phthalate. However, the polyolefins obtained by using such catalyst shows rather low yield. WO2006/056338A1 discloses a process for the polymerization of propylene using a catalyst comprising a catalyst component obtained by a process wherein a compound with formula $Mg(OAlk)_xCl_y$ wherein x is larger than 0 and smaller than 2, y equals 2-x and each Alk, independently, represents an alkyl group, is contacted with a titanium tetraalkoxide and/or an alcohol in the presence of an inert dispersant to give an intermediate reaction product and wherein the intermediate reaction product is contacted with titanium tetrachloride in the presence of an internal donor, which is dibutyl phthalate. However, polyolefins with narrow MWD are obtained by applying the catalyst disclosed in this document. EP1838741B1 discloses a process for producing a catalyst for the polymerization of an olefin, wherein a compound with formula $Mg(OAlk)_xCl_y$, wherein x is larger than 0 and smaller than 2, y equals 2-x and each Alk, independently, represents an alkyl group, is contacted with a titanium tetraalkoxide and/or an alcohol in the presence of an inert dispersant to give an intermediate reaction product and wherein the intermediate reaction product is contacted with titanium tetrachloride in the presence of an internal donor. However, polyolefins with narrow MWD are obtained with the catalyst disclosed in EP1838741B1. The molecular weight distribution (MWD) influences the properties of polyolefins and as such influences the end-uses of a polymer; broad MWD generally improves the flowability at high shear rate during the processing and the processing of polyolefins in applications requiring fast processing at fairly high die swell, such as in blowing and extrusion techniques.

WO2011/106497 of Dow discloses a procatalyst composition comprising: a combination of a magnesium moiety, a titanium moiety and an internal electron donor comprising a certain halogenated amide ester, viz. $(Ar_1COOC(R_3,R_4)C(R_1,R_2)C(R_5,R_6)NHCOAr_2$, having a hydrogen substituent on the amide nitrogen.

There is, however, an on-going need in industry for catalysts showing better performance, e.g. higher activity, good control of stereochemistry, higher isotacticity, higher hydrogen sensitivity and/or allowing obtaining polyolefins in higher yield and/or having broader molecular weight distribution.

It is thus an object of the invention to provide an improved catalyst composition for polymerization of olefins, especially polypropylene that allows obtaining of polyolefins with broader molecular weight distribution and higher yield while maintaining good isotacticity.

This object is achieved with a catalyst composition for polymerization of olefins, which comprises a monoester and an internal donor being a compound represented by formula (I),

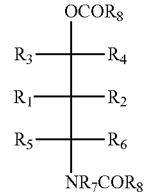

Formula (I)

wherein:

$R_1$, $R_2$, $R_3$, $R_4$, $R_5$ and $R_6$ are the same or different and are independently selected from the group consisting of hydrogen, straight, branched and cyclic alkyl having at most 20 carbon atoms and aromatic substituted and unsubstituted hydrocarbyl having 6 to 20 carbon atoms;

$R_7$ is selected from the group consisting of straight, branched and cyclic alkyl having at most 20 carbon atoms and aromatic substituted and unsubstituted hydrocarbyl having 6 to 20 carbon atoms; and $R_8$ is selected from the group consisting of aromatic substituted and unsubstituted hydrocarbyl having 6 to 20 carbon atoms.

It has been surprisingly found that the catalyst composition that comprises a monoester and an internal electron donor compound having formula (I) allows preparation of polyolefins, particularly of polypropylenes (PP) that have broader molecular weight distribution, higher polymer yield and good stereospecificity, i.e. high isotacticity. Polyolefins having broad molecular weight distribution are herein polyolefins, e.g. polypropylene having a Mw/Mn higher than 6.5 or higher than 7 or even higher than 8, a broad molecular weight distribution being desirable in the development of different grades of polymer used in certain applications, such as thermoforming, pipes, foams, films, blow-molding. The amount of amorphous atactic polymer in the products obtained (e.g. polypropylene), such as for example at most 3 wt % or at most 2 wt % or even lower than 1 wt % of the total amount of polymer, denoting high isotacticity.

A further advantage of the present invention is that low amount of wax is formed, i.e. low molecular weight polymers during the polymerization reaction, which results in reduced or no "stickiness" on the inside walls of the polymerization reactor and inside the reactor. In addition, the catalyst composition according to the present invention can also be phthalate-free allowing obtaining non-toxic polyolefins, which show no harmful effects on human health and which thus can be used for instance in food and medical industry. Moreover, a lower amount (2-3 times) of the compound of formula (I) is required when the monoester is also used compared with when only the compound of formula (I) and no monoester is used in the catalyst composition. Furthermore, the catalyst composition according to the present invention has higher hydrogen sensitivity (higher MFR).

SUMMARY OF THE PRESENT INVENTION

The present invention relates in a first aspect to a catalyst composition for polymerization of olefins comprising a monoester and an internal electron donor represented by formula (I) above, wherein: $R_1$, $R_2$, $R_3$, $R_4$, $R_5$ and $R_6$ are the same or different and are independently selected from the group consisting of hydrogen, straight, branched and cyclic alkyl having at most 20 carbon atoms and aromatic substituted and unsubstituted hydrocarbyl having 6 to 20 carbon atoms; $R_7$ is selected from the group consisting of straight, branched and cyclic alkyl having at most 20 carbon atoms and aromatic substituted and unsubstituted hydrocarbyl having 6 to 20 carbon atoms; and $R_8$ is selected from the group consisting of aromatic substituted and unsubstituted hydrocarbyl having 6 to 20 carbon atoms.

In an embodiment, $R_1$, $R_2$, $R_3$, $R_4$, $R_5$ and $R_6$ are independently selected from the group consisting of hydrogen, methyl, ethyl, propyl, isopropyl, butyl, tert-butyl, phenyl, trifluoromethyl and halophenyl group.

In another embodiment $R_1$ and $R_2$ are each a hydrogen atom.

In another embodiment, when one of $R_3$ and $R_4$ has at least one carbon atom then the other one of $R_3$ and $R_4$ is hydrogen and wherein when $R_5$ and $R_6$ has at least one carbon atom then the other one of $R_5$ and $R_6$ is a hydrogen atom.

In another embodiment, $R_7$ is selected from a group consisting of methyl, ethyl, propyl, isopropyl, butyl, tert-butyl, phenyl, benzyl, substituted benzyl and halophenyl group.

In another embodiment, $R_8$ is substituted or unsubstituted phenyl, benzyl, naphthyl, ortho-tolyl, para-tolyl or anisol group.

In another embodiment, the monoester is an acetate or a benzoate, preferably ethyl acetate, amyl acetate or ethyl benzoate.

In another embodiment, the catalyst comprises a magnesium-containing support, a halogen-containing titanium compound, said monoester and said internal electron donor according to formula (I).

In another embodiment, the catalyst composition further comprises an additional internal electron donor selected from the group consisting of diesters and diethers, preferably dibutyl phthalate or 9,9-bis-methoxymethyl-fluorene.

In another embodiment, the catalyst composition further comprises an additional internal electron donor selected from the group consisting of diesters and diethers, preferably dibutyl phthalate or 9,9-bis-methoxymethyl-fluorene, wherein the molar ratio of the additional internal electron donor to magnesium of said magnesium-containing support is between 0.02 and 0.15.

In another aspect, the present invention relates to a process for preparing the catalyst composition, said process comprising contacting a magnesium-containing support with a halogen-containing titanium compound, a monoester, a first internal electron donor represented by formula (I), and optionally a second internal electron donor selected from a group consisting of diesters and diethers, wherein: $R_1$, $R_2$, $R_3$, $R_4$, $R_5$ and $R_6$ are the same or different and are independently selected from the group consisting of hydrogen, straight, branched and cyclic alkyl having at most 20 carbon atoms and aromatic substituted and unsubstituted hydrocarbyl having 6 to 20 carbon atoms; $R_7$ is selected from the group consisting of straight, branched and cyclic alkyl having at most 20 carbon atoms and aromatic substituted and unsubstituted hydrocarbyl having 6 to 20 carbon atoms; and $R_8$ is selected from the group consisting of aromatic substituted and unsubstituted hydrocarbyl having 6 to 20 carbon atoms.

In an embodiment, said process comprises the steps of:
i) contacting a compound $R^9_z MgX_{2-z}$ wherein $R^9$ is aromatic, aliphatic or cyclo-aliphatic group containing 1 to 20 carbon atoms, X is a halide, and z is in a range of larger than 0 and smaller than 2, with an alkoxy- or aryloxy-containing silane compound to give a first intermediate reaction product;
ii) contacting the first intermediate reaction product with at least one activating compound selected from the group formed by electron donors and compounds of formula $M(OR^{10})_{v-w}(OR^{11})_w$, wherein M can be Ti, Zr, Hf, Al or Si, and $M(OR^{10})_{v-w}(R^{11})_w$, wherein M is Si, each $R^{10}$ and $R^{11}$, independently, represent an alkyl, alkenyl or aryl group, v is the valency of M, v being either 3 or 4, and w is smaller than v; preferably the at least one activation compound is selected from the group formed by compounds of formula $M(OR^{10})_{v-w}(R^{11})_w$, wherein M is Si, to give a second intermediate reaction product; and
iii) contacting the second intermediate reaction product with a halogen-containing Ti-compound, the monoester, the compound represented by formula (I) as the first internal electron donor, and optionally the diester or diether as the second internal electron donor.

In another aspect, the present invention relates to a catalyst composition obtained by or obtainable by the process according to the present invention.

In another aspect, the present invention relates to polymerization catalyst system comprising the catalyst composition according to the present invention or the catalyst composition obtained by or obtainable by the process of the present invention, a co-catalyst and optionally an external electron donor.

In another aspect, the present invention relates to process of making a polyolefin comprising a step of contacting an olefin with the present catalyst system, the olefin being preferably propylene.

In another aspect, the present invention relates to the use of the present catalyst composition comprising a monoester, a compound represented by formula (I) as a first internal electron donor, and optionally a second internal electron donor selected from a group consisting of diesters and diethers in the polymerization of olefins, wherein: $R_1$, $R_2$, $R_3$, $R_4$, $R_5$ and $R_6$ are the same or different and are independently selected from the group consisting of hydrogen, straight, branched and cyclic alkyl having at most 20 carbon atoms and aromatic substituted and unsubstituted hydrocarbyl having 6 to 20 carbon atoms; $R_7$ is selected from the group consisting of straight, branched and cyclic alkyl having at most 20 carbon atoms and aromatic substituted and unsubstituted hydrocarbyl having 6 to 20 carbon atoms; and $R_8$ is selected from the group consisting of aromatic substituted and unsubstituted hydrocarbyl having 6 to 20 carbon atoms.

DEFINITIONS

An internal donor (also referred to as internal electron donor) is herein defined as an electron-donating compound that is commonly described in prior art as a reactant in the preparation of a solid catalyst component for a Ziegler-Natta catalyst system for olefins polymerization; i.e. contacting a magnesium-containing support with a halogen-containing Ti compound and an internal donor.

As used herein, the term "hydrocarbyl" is a substituent containing only hydrogen or carbon atoms, including linear or branched, saturated or unsaturated aliphatic radical, such as alkyl, alkenyl, and alkynyl; alicyclic radical, such as cycloalkyl, cycloalkenyl; aromatic radical, such as monocyclic or polycyclic aromatic radical, as well as combinations thereof, such as alkaryl and aralkyl.

As described therein, the term "substituted hydrocarbyl" is a hydrocarbyl group that is substituted with one or more nonhydrocarbyl substituent groups. A nonlimiting example of a nonhydrocarbyl substituent is a heteroatom. As used herein, a hydrocarbon is an atom other than carbon or hydrogen. Non-limiting examples of heteroatoms include: halogens (F, Cl, Br, I), N, O, P, B, S and Si.

DETAILED DESCRIPTION OF THE INVENTION

The present invention will be discussed in more detail below.

The monoester according to the present invention can be any ester of a monocarboxylic acid known in the art. The monoester can have the formula R'—CO—OR", wherein R' can be the same or different from R".

R' may be selected from the group consisting of hydrogen, straight, branched and cyclic alkyl having at most 20 carbon atoms and aromatic substituted and unsubstituted hydrocarbyl having 6 to 20 carbon atoms. Particularly, R' may be selected from the group consisting of hydrogen; straight and branched alkyl having 1 to 20 carbon atoms, preferably 1 to 10 carbon atoms and most preferably 1 to 5 carbon atoms; and cyclic alkyl having 3 to 20 carbon atoms, preferably 3 to 10 carbon atoms and most preferably 3 to 5 carbon atoms; and aromatic substituted and unsubstituted hydrocarbyl having 6 to 20 carbon atoms, preferably 6 to 10 carbon atoms.

R" may be selected from the group consisting of straight, branched and cyclic alkyl having at most 20 carbon atoms and aromatic substituted and unsubstituted hydrocarbyl having 6 to 20 carbons. Particularly, the monoester can have the formula R'—CO—OR", wherein R' can be the same or different from R" and wherein R' may be selected from the group consisting of hydrogen; straight and branched alkyl having 1 to 20 carbon atoms, preferably 1 to 10 carbon atoms and most preferably 1 to 5 carbon atoms; and cyclic alkyl having 3 to 20 carbon atoms, preferably 3 to 10 carbon atoms and most preferably 3 to 5 carbon atoms; and aromatic substituted and unsubstituted hydrocarbyl having 6 to 20 carbon atoms, preferably 6 to 10 carbon atoms.

Suitable examples of monoesters include formates, for instance, butyl formate; acetates, for instance ethyl acetate, amyl acetate and butyl acetate; acrylates, for instance ethyl acrylate, methyl methacrylate and isobutyl methacrylate; benzoates, particularly C1-C20 hydrocarbyl esters of benzoic acid, wherein the hydrocarbyl group is substituted or unsubstituted with one or more Group 14, 15 or 16 heteroatom containing substituents and C1-C20 (poly)hydrocarbyl ether derivatives thereof, preferably, C1-C4 alkyl benzoate and C1-C4 ring alkylated derivatives thereof; more preferably, methyl benzoate, ethyl benzoate, propyl benzoate, methyl p-methoxy benzoate, methyl p-ethoxy benzoate; most preferably ethyl benzoate. Other suitable examples include methyl-p-toluate and ethyl-naphthate. More preferably, the monoester is an acetate or a benzoate. Most preferably, the monoester is ethyl acetate, amyl acetate or ethyl benzoate.

Preferably, $R_1$, $R_2$, $R_3$, $R_4$, $R_5$ and $R_6$ in Formula (I) are independently selected from a group consisting of hydrogen; straight and branched alkyl with 1 to 10 carbon atoms; and cyclic alkyl with 3 to 10 carbon atoms; and aromatic substituted and unsubstituted hydrocarbyl having 6 to 10 carbon atoms. More preferably, $R_1$, $R_2$, $R_3$, $R_4$, $R_5$ and $R_6$ are independently selected from a group of compounds consisting of hydrogen, $C_1$-$C_{10}$ straight and branched alkyl; $C_3$-$C_{10}$ cycloalkyl; $C_6$-$C_{10}$ aryl; and $C_7$-$C_{10}$ alkaryl and aralkyl group. Even more preferably, $R_1$, $R_2$, $R_3$, $R_4$, $R_5$ and $R_6$ are independently selected from a group consisting of hydrogen, methyl, ethyl, propyl, isopropyl, butyl, tert-butyl, phenyl, trifluoromethyl and halophenyl group. Most preferably, $R_1$, $R_2$, $R_3$, $R_4$, $R_5$ and $R_6$ are each hydrogen, methyl, ethyl, propyl, phenyl or trifluoromethyl.

Preferably, $R_1$ and $R_2$ are each a hydrogen atom. More preferably, $R_1$ and $R_2$ are each a hydrogen atom and each of $R_3$, $R_4$, $R_5$ and $R_6$ is selected from the group consisting of hydrogen, $C_1$-$C_{10}$ straight and branched alkyl; $C_3$-$C_{10}$ cycloalkyl; $C_6$-$C_{10}$ aryl; and $C_7$-$C_{10}$ alkaryl and aralkyl group; even more preferably, $R_3$, $R_4$, $R_5$ and $R_6$ are each selected from the group consisting of hydrogen, methyl, ethyl, propyl, isopropyl, butyl, tert-butyl, phenyl, trifluoromethyl and halophenyl group; most preferably, $R_3$, $R_4$, $R_5$ and $R_6$ are each hydrogen, methyl, ethyl, propyl, phenyl or trifluoromethyl.

Preferably, at least one of $R_3$ and $R_4$ and at least one of $R_5$ and $R_6$ is having at least one carbon atom, as defined above. More preferably, when one of $R_3$ and $R_4$ has at least one carbon atom then the other one of $R_3$ and $R_4$ is hydrogen and wherein when one of $R_5$ and $R_6$ has at least one carbon atom then the other one of $R_5$ and $R_6$ is hydrogen.

Preferably, $R_7$ in Formula (I) is the same or different than any of $R_1$, $R_2$, $R_3$, $R_4$, $R_5$ and $R_6$ with the provision that $R_7$ is not a hydrogen atom.

Preferably, $R_7$ is selected from the group consisting of straight and branched alkyl having 1 to 10 carbon atoms; and cyclic alkyl having 3 to 10 carbon atoms; and aromatic substituted and unsubstituted hydrocarbyl having 6 to 10 carbon atoms. More preferably, $R_7$ is selected from a group consisting of $C_1$-$C_{10}$ straight and branched alkyl; $C_3$-$C_{10}$ cycloalkyl; $C_6$-$C_{10}$ aryl; and $C_7$-$C_{10}$ alkaryl and aralkyl group. Even more preferably, $R_7$ is selected from a group consisting of methyl, ethyl, propyl, isopropyl, butyl, tert-butyl, phenyl, benzyl and substituted benzyland halophenyl group. Most preferably, $R_7$ is methyl, ethyl, propyl, isopropyl, benzyl orphenyl; and even most preferably, $R_7$ is methyl, ethyl or propyl.

$R_8$ in Formula (I) can be the same or different than each of $R_1$-$R_7$ and is preferably an aromatic substituted and unsubstituted hydrocarbyl having 6 to 10 carbon atoms. More preferably, $R_8$ is selected from the group consisting of $C_6$-$C_{10}$ aryl unsubstituted or substituted with e.g. an acyl-halide or an alkoxyde; and $C_7$-$C_{10}$ alkaryl and aralkyl group; for instance, 4-methoxyphenyl, 4-chlorophenyl, 4-methylphenyl. Particularly preferred, $R_8$ is substituted or unsubstituted phenyl, benzyl, naphthyl, ortho-tolyl, para-tolyl oranisol group. Most preferably, $R_8$ is phenyl.

Preferably, $R_1$ and $R_2$ are each a hydrogen atom and one of $R_3$ and $R_4$ and one of $R_5$ and $R_6$ is selected from the group consisting of $C_1$-$C_{10}$ straight and branched alkyl; $C_3$-$C_{10}$ cycloalkyl; $C_6$-$C_{10}$ aryl; and $C_7$-$C_{10}$ alkaryl and aralkyl group; more preferably, methyl, ethyl, propyl, isopropyl, butyl, tert-butyl, phenyl, trifluoromethyl and halophenyl group; and most preferably, one of $R_3$ and $R_4$ and one of $R_5$ and $R_6$ is methyl.

The compound represented by Formula (I) can be also referred herein to as the "first internal electron donor".

The catalyst composition according to the present invention may further comprise an additional internal electron donor, herein also referred to as the "second internal electron donor". The additional internal donor is selected from a group consisting of diesters and diethers.

The diester can be any ester of a C6-C20 aromatic dicarboxylic acid or a C1-C20 aliphatic dicarboxylic acid known in the art. Suitable examples of diesters include C6-C20 aromatic or C1-C20 aliphatic substituted phthalates, e.g. dibutyl phthalate, diisobutyl phthalate, diallyl phthalate and/or diphenyl phthalate; C6-C20 aromatic or C1-C20 aliphatic substituted succinates; and also C6-C20 aromatic or C1-C20 aliphatic substituted esters of malonic acid or glutaric acid. Preferably the diester is a C1-C10 aliphatic substituted phthalate, more preferably dibutyl phthalate.

The diether can be any diether known in the art. Suitable diether examples include C6-C20 aromatic and C1-C20 aliphatic substituted diethers, e.g. 2,2-diisobutyl-1,3-dimethoxypropane, 2,2-dicyclopentyl-1,3-dimethoxypropane, 2-ethyl-2-butyl-1,3-dimethoxypropane, 2-isopropyl-2-isopentyl-1,3-dimethoxypropane, 1,1-bis(methoxymethyl)cyclopentadiene, 1,1-bis(methoxymethyl)-2,3,4,5-tetramethylcyclopentadiene; 1,1-bis(methoxymethyl)-2,3,4,5-tetraphenylcyclopentadiene; 1,1-bis(methoxymethyl) indene; 1,1-bis(methoxymethyl)-2,3-dimethylindene; 1,1-bis(methoxymethyl)cyclopenthylindene; 9,9-bis(methoxymethyl) fluorene; 9,9-bis(methoxymethyl)-2,3,6,7-tetramethylfluorene; 9,9-bis(methoxymethyl)-2,3-benzofluorene; 9,9-bis(methoxymethyl)-2,7-diisopropylfluorene; 9,9-bis(methoxymethyl)-1,8-dichlorofluorene; 9,9-bis(methoxymethyl)-2,7-dicyclopentylfluorene; 9,9-bis(methoxymethyl) difluorofluorene; 9,9-bis(methoxymethyl)-1,2,3,4-tertrahydrofluorene; 9,9-bis(methoxymethyl)-4-tert-butylfluorene. Preferably, the diether is 9,9-bis-methoxymethyl-fluorene.

The catalyst composition according to the present invention can be the solid catalyst component of a Ziegler-Natta type of catalyst system as known in the art, also known under the term of "procatalyst" and which typically comprises a magnesium-containing support, a halogen-containing titanium compound and an internal electron donor. Such catalyst systems are already described in the prior art, for instance in documents WO96/32426A, WO2006/056338A1, EP1838741B1 and U.S. Pat. No. 5,077,357.

According to the present invention, the catalyst composition comprises a magnesium-containing support, a halogen-containing titanium compound, a monoester, an internal electron donor represented by formula (I), and optionally an additional internal electron donor selected from a group consisting of diesters and diethers.

Preferably, the catalyst composition of present invention consists of a magnesium-containing support, a halogen-containing titanium compound, a monoester, an internal electron donor represented by formula (I), and optionally an additional internal electron donor selected from a group consisting of diesters and diethers.

Without being limited thereto, particular examples of the compounds of formula (I) are the structures as depicted in formulas (II)-(XII). For instance, the structure in Formula (II) correspond to 4-[benzoyl(methyl)amino]pentan-2-yl benzoate]; Formula (III) to 3-[benzoyl(cyclohexyl)amino]-1-phenylbutyl benzoate; Formula (IV) to 3-[benzoyl(propan-2-yl)amino]-1-phenylbutyl benzoate; Formula (V) to 4-[benzoyl(propan-2-yl)amino]pentan-2-yl benzoate; Formula (VI) to 4-[benzoyl(methyl)amino]-1,1,1-trifluoropentan-2-yl benzoate; Formula (VII) to 3-(methylamino)-1,3-diphenylpropan-1-oldibenzoate; Formula (VIII) to 2,2,6,6-tetramethyl-5-(methylamino)heptan-3-ol dibenzoate; Formula (IX) to 4-(ethyl)aminopentan-2-yl dibenzoate; Formula (X) to 3-(methyl)amino-propan-1-ol dibenzoate; Formula (XI) to 3-(methyl)amino-2,2-dimethylpropan-1-ol dibenzoate; Formula (XII) to 4-(methylamino)pentan-2-yl bis (4-methoxy)benzoate). The compound of formula (II) is one of the preferred first internal electron donors in the catalyst composition according to the present invention as it has high catalytic activity and it allows preparation of polyolefins having molecular weight distribution broader than 7, high isotacticity and with high yield.

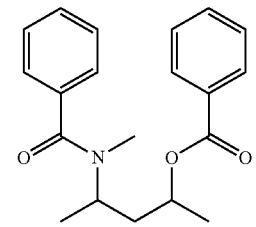

Formula (II)

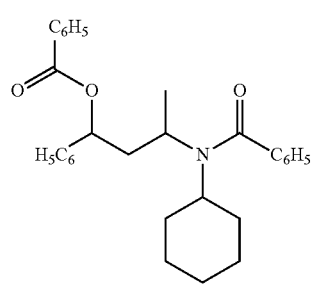

Formula (III)

-continued

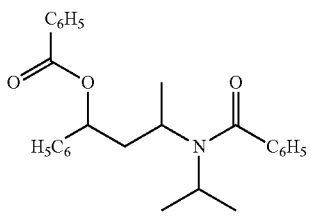
Formula (IV)

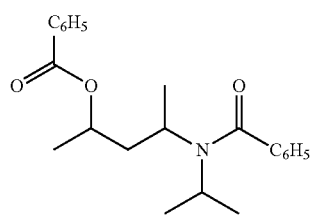
Formula (V)

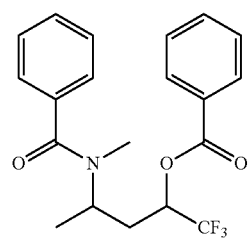
Formula (VI)

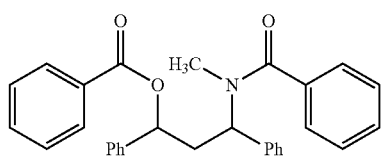
Formula (VII)

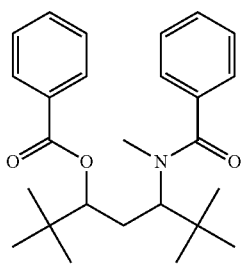
Formula (VIII)

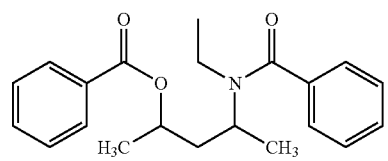
Formula (IX)

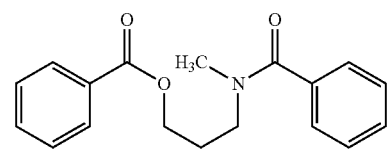
Formula (X)

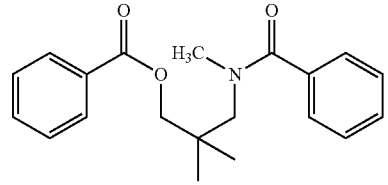
Formula (XI)

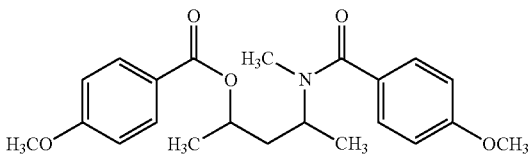
Formula (XII)

The compound according to formula (I) can be made by any method known in the art. In this respect, reference is made to J. Chem. Soc. Perkin trans. 1 1994, 537-543 and to Org. Synth. 1967, 47, 44. These documents disclose a step a) of contacting a substituted 2,4-diketone with a substituted amine in the presence of a solvent to give a beta-enaminoketone; followed by a step b) of contacting the beta-enaminoketone with a reducing agent in the presence of a solvent to give a gamma-aminoalcohol. The substituted 2,4-diketone and the substituted amine can be applied in step a) in amounts ranging from 0.5 to 2.0 mole, preferably from 1.0 to 1.2 mole. The solvent in steps a) and b) may be added in an amount of 5 to 15 volume, based on the total amount of the diketone, preferably of 3 to 6 volume. The beta-enaminoketone to diketone mole ratio in step b) may be of from 0.5 to 6, preferably from 1 to 3. The reducing agent to beta-enaminoketone mole ratio in step b) may be of from 3 to 8, preferably from 4 to 6; the reducing agent may be selected from the group comprising metallic sodium, NaBH$_4$ in acetic acid, Ni—Al alloy. Preferably, the reducing agent is metallic sodium because it is a cheap reagent.

The gamma-aminoalcohol that can be used for making compound (I) can be synthesized as described in the literature and also mentioned herein above or this compound can be directly purchased commercially and used as a starting compound in a reaction to obtain the compound represented by formula (I). Particularly, the gamma-aminoalcohol can be reacted with a substituted or unsubstituted benzoyl chloride in the presence of a base to obtain the compound represented by formula (I) (referred herein also as step c), regardless that gamma-aminoalcohol was synthesized as described in the literature or commercially purchased). The molar ratio between the substituted or unsubstituted benzoyl chloride and the gamma-aminoalcohol may range from 2 to 4, preferably from 2 to 3. The base may be any basic chemical compound that is able to deprotonate the gamma-aminoalcohol. Said base can have a pK$_a$ of at least 5; or at least 10 or preferably between 5 and 40, wherein pK$_a$ is a constant already known to the skilled person as the negative logarithm of the acid dissociation constant k$_a$. Preferably, the base is pyridine; a trialkyl amine, e.g. triethylamine; or a metal hydroxide e.g. NaOH, KOH. Preferably, the base is pyridine. The molar ratio between the base and the gamma-aminoalcohol may range from 3 to 10, preferably from 4 to 6.

The solvent used in any of steps a), b) and c) can be selected from any organic solvents, such as toluene, dichloromethane, 2-propanol, cyclohexane or mixtures of any organic solvents. Preferably, toluene is used in each of steps a), b) and c). More preferably, a mixture of toluene and 2-propanol is used in step b). The solvent in step c) can be added in an amount of 3 to 15 volume, preferably from 5 to 10 volume based on the gamma-aminoalcohol.

The reaction mixture in any of steps a), b) and c) may be stirred by using any type of conventional agitators for more than about 1 hour, preferably for more than about 3 hours and most preferably for more than about 10 hours, but less than about 24 hours. The reaction temperature in any of steps a) and b) may be the room temperature, i.e. of from about 15 to about 30° C., preferably of from about 20 to about 25° C. The reaction temperature in step c) may range between 0 and 10° C., preferably between 5 and 10° C. The reaction mixture in any of steps a), b) and c) may be refluxed for more than about 10 hours, preferably for more than about 20 hours but less than about 40 hours or until the reaction is complete (reaction completion may be measured by Gas Chromatography, GC). The reaction mixture of steps a) and b) may be then allowed to cool to room temperature, i.e. at a temperature of from about 15 to about 30° C., preferably of from about 20 to about 25° C. The solvent and any excess of components may be removed in any of steps a), b) and c) by any method known in the art, such as evaporation, washing. The obtained product in any of steps b) and c) can be separated from the reaction mixture by any method known in the art, such as by extraction over metal salts, e.g. sodium sulphate.

The process for preparing the catalyst composition according to the present invention comprises contacting a magnesium-containing support with a halogen-containing titanium compound, a monoester, a compound represented by formula (I) as a first internal electron donor and optionally, a second internal electron donor selected from a group consisting of diesters and diethers.

The magnesium-containing support, halogen-containing titanium compounds and internal electron donor(s) used in the process according to the present invention are known in the art as typical components of a Ziegler-Natta catalyst composition, particularly of the solid component of a Ziegler-Natta catalyst system. Any magnesium-containing support and any halogen-containing titanium compounds known in the art can be used in the process according to the present invention. For instance, synthesis of such titanium-magnesium based catalyst compositions with different magnesium-containing support-precursors, such as magnesium halides, magnesium alkyls and magnesium aryls, and also magnesium alkoxy and magnesium aryloxy compounds for polyolefin production, particularly of polypropylenes production are described for instance in U.S. Pat. No. 4,978,648, WO96/32427A1, WO01/23441 A1, EP1283 222A1, EP1222 214B1; U.S. Pat. No. 5,077,357; U.S. Pat. No. 5,556,820; U.S. Pat. No. 4,414,132; U.S. Pat. No. 5,106,806 and U.S. Pat. No. 5,077,357 but the present process is not limited to the disclosure in these documents.

Preferably, the process for preparing the catalyst composition according to the present invention comprises the steps of:
i) contacting a compound $R^9_z MgX_{2-z}$ wherein $R^9$ is aromatic, aliphatic or cyclo-aliphatic group containing at most 20 carbon atoms, X is a halide, and z is in a range of larger than 0 and smaller than 2, with an alkoxy- or aryloxy-containing silane compound to give a first intermediate reaction product;
ii) contacting the first intermediate reaction product with at least one activating compound selected from the group formed by electron donors and compounds of formula $M(OR^{10})_{v-w}(OR^{11})_w$, wherein M can be Ti, Zr, Hf, Al or Si, and $M(OR^{10})_{v-w}(R^{11})_w$, wherein M is Si, each $R^{10}$ and $R^{11}$, independently, represent an alkyl, alkenyl or aryl group, v is the valency of M, v being either 3 or 4 and w is smaller than v to give a second intermediate reaction product; and
iii) contacting the second intermediate reaction product with a halogen-containing Ti-compound, the monoester, the compound represented by formula (I) as the first internal electron donor and optionally, the second internal electron donor selected from the group consisting of diesters and diethers.

This preferred process to prepare the catalyst composition according to the present invention results in catalyst compositions that allow obtaining polyolefins, particularly polypropylenes in high yield and having broad molecular weight distribution and high isotacticity.

In an embodiment, the process for preparing the catalyst composition according to the present invention comprises the steps of:
i) contacting a compound $R^9_z MgX_{2-z}$ wherein $R^9$ is aromatic, aliphatic or cyclo-aliphatic group containing at most 20 carbon atoms, X is a halide, and z is in a range of larger than 0 and smaller than 2, with an alkoxy- or aryloxy-containing silane compound to give a first intermediate reaction product;
ii) contacting the first intermediate reaction product with at least one activating compound selected from the group formed by compounds of formula $M(OR^{10})_{v-w}(R^{11})_w$, wherein M is Si, each $R^{10}$ and $R^{11}$, independently, represent an alkyl, alkenyl or aryl group, v is the valency of M, v being either 3 or 4 and w is smaller than v to give a second intermediate reaction product; and
iii) contacting the second intermediate reaction product with a halogen-containing Ti-compound, the monoester, the compound represented by formula (I) as the first internal electron donor and optionally, the second internal electron donor selected from the group consisting of diesters and diethers.

This preferred process to prepare the catalyst composition according to the present invention results in catalyst compositions that allow obtaining polyolefins, particularly polypropylenes in high yield and having broad molecular weight distribution and high isotacticity.

Step i)

In step i) a first intermediate reaction product, i.e. a solid magnesium-containing support is prepared by contacting a compound or a mixture of compounds of formula $R^9_z MgX_{2-z}$ wherein $R^9$ is aromatic, aliphatic or cyclo-aliphatic group containing at most 20 carbon atom, X is a halide, and z is larger than 0 and smaller than 2, with an alkoxy- or aryloxy-containing silane compound, as for example described in WO 96/32427 A1 and WO01/23441 A1. In the compound $R^9_z MgX_{2-z}$, also referred to as Grignard compound, X is preferably chlorine or bromine, more preferably chlorine.

Preferably, $R^9$ can be an aliphatic group having 1 to 20 carbon atoms, preferably 1 to 10 carbon atoms and more preferably 1 to 5 carbon atoms. $R^9$ can also be an aromatic group having 6 to 20 carbon atoms, preferably 6 to 10 carbon atoms or cyclo-aliphatic group containing 3 to 20 carbon atoms, preferably 3 to 10 carbon atoms. $R^9$ can be an alkyl, aryl, aralkyl, alkoxide, phenoxide, etc., or mixtures thereof with at most 20 carbon atoms, preferably at most 10 carbon atoms. Suitable examples of group $R^9$ are methyl, ethyl, n-propyl, i-propyl, n-butyl, i-butyl, t-butyl, hexyl, cyclohexyl, octyl, phenyl, tolyl, xylyl, mesityl and benzyl. In a preferred embodiment of the invention, $R^9$ represents an aromatic group, for instance a phenyl group. The Grignard compound of formula $R^9_z MgX_{2-z}$, wherein z is larger than 0 and smaller than 2, is preferably characterized by z being from about 0.5 to 1.5.

The alkoxy- or aryloxy-containing silane used in step i) is typically a compound or a mixture of compounds with the general formula $Si(OR^{13})_{4-n}R^{14}_n$, wherein n can range from 0 up to 3, preferably n is from 0 up to and including 1, and wherein each $R^{13}$ and $R^{14}$ groups, independently, represent an alkyl, alkenyl or aryl group, optionally containing one or more hetero atoms for instance O, N, S or P, with, for instance, 1-20 C-atoms. Examples of suitable silane-compounds include tetramethoxysilane, tetraethoxysilane, methyltrimethoxysilane, methyltributoxysilane, phenyltriethoxysilane. Preferably, tetraethoxysilane is used as silane-compound in preparing the solid Mg-containing compound in the process according to the invention. Preferably, in step i) the silane-compound and the Grignard compound are introduced simultaneously to a mixing device to result in particles of advantageous morphology, especially of the larger particles, as described in WO 01/23441 A1. Here, 'morphology' does not only refer to the shape of the particles of the solid Mg-compound and the catalyst made therefrom, but also to the particle size distribution (also characterized as span), its fines content, powder flowability, and the bulk density of the catalyst particles. Moreover, it is well known that a polyolefin powder produced in polymerization process using a catalyst system based on such catalyst component has a similar morphology as the catalyst component (the so-called "replica effect"; see for instance S. van der Ven, Polypropylene and other Polyolefins, Elsevier 1990, p. 8-10). Accordingly, almost round polymer particles are obtained with a length/diameter ratio (l/D) smaller than 2 and with good powder flowability. Introduced simultaneously means that the introduction of the Grignard compound and the silane-compound is done in such way that the molar ratio Mg/Si does not substantially vary during the introduction of these compounds to the mixing device, as described in WO 01/23441 A1. The silane-compound and Grignard compound can be continuously or batch-wise introduced to the mixing device. Preferably, the both compounds are introduced continuously to a mixing device.

It is explicitly noted that it is possible that the Grignard compound in step i) may alternatively have a different structure, for example, may be a complex. Such complexes are already known to the skilled person in the art; a particular example of such complexes is Phenyl$_4$Mg$_3$Cl$_2$.

The mixing device can have various forms; it can be a mixing device in which the silane-compound is premixed with the Grignard compound, the mixing device can also be a stirred reactor, in which the reaction between the compounds takes place. Preferably, the compounds are premixed before the mixture is introduced to the reactor for step i). In this way, a catalyst component is formed with a morphology that leads to polymer particles with the best morphology (high bulk density, narrow particle size distribution, (virtually) no fines, excellent flowability). The Si/Mg molar ratio during step i) may vary within wide limits for instance from 0.2 to 20. Preferably, the Si/Mg molar ratio is from 0.4 to 1.0.

The period of premixing in above indicated reaction step may vary between wide limits, for instance 0.1 to 300 seconds. Preferably premixing is performed during 1 to 50 seconds.

The temperature during the premixing step is not specifically critical, and may for instance range between 0 and 80° C.; preferably the temperature is between 10° C. and 50° C. The reaction between said compounds may, for instance, take place at a temperature between −20° C. and 100° C.; preferably at a temperature of from 0° C. to 80° C.

The first intermediate reaction product obtained from the reaction between the silane compound and the Grignard compound is usually purified by rinsing with an inert solvent, for instance a hydrocarbon solvent with for example 1-20 C-atoms, like pentane, iso-pentane, hexane or heptane. The solid product can be stored and further used as a suspension in said inert solvent. Alternatively, the product may be dried, preferably partly dried, and preferably under mild conditions; e.g. at ambient temperature and pressure.

The first intermediate reaction product obtained by this step i) may comprise a compound of the formula Mg(OR$^{13}$)$_x$X$_{2-x}$, wherein the group R$^{13}$ is an alkyl group containing 1-12 carbon atoms or an aryl group containing 6-12 carbon atoms, although the present invention is not limited thereby. X is a halide, and x is larger than 0 and smaller than 2, preferably between 0.5 and 1.5. Preferably, X is chlorine or bromine and more preferably, X is chlorine.

Preferably, the R$^{13}$ group contains 1-8 carbon atoms. More preferably, at least one of the R$^{13}$-groups represents an ethyl group. In a preferred embodiment, each R$^{13}$-group represents an ethyl group.

R$^9_z$MgX$_{2-z}$ used in step i) may be prepared by contacting metallic magnesium with an organic halide R$^9$X, as described in WO 96/32427 A1 and WO01/23441 A1. All forms of metallic magnesium may be used, but preferably use is made of finely divided metallic magnesium, for example magnesium powder. To obtain a fast reaction it is preferable to heat the magnesium under nitrogen prior to use. R$^9$ and X have the same meaning as described above. Combinations of two or more organic halides R$^9$X can also be used.

The magnesium and the organic halide R$^9$X can be reacted with each other without the use of a separate dispersant; the organic halide R$^9$X is then used in excess. The organic halide R$^9$X and the magnesium can also be brought into contact with one another and an inert dispersant. Examples of these dispersants are: aliphatic, alicyclic or aromatic dispersants containing at most 20 carbon atoms, preferably from 4 or 6 up to 20 carbon atoms.

Preferably, in this step of preparing R$^9_z$MgX$_{2-z}$, also an ether is added to the reaction mixture. Examples of ethers are: diethyl ether, diisopropyl ether, dibutyl ether, diisobutyl ether, diisoamyl ether, diallyl ether, tetrahydrofuran and anisole. Dibutyl ether and/or diisoamyl ether are preferably used. Preferably, an excess of chlorobenzene is used as the organic halide R$^9$X. Thus, the chlorobenzene serves as dispersant as well as organic halide R$^9$X.

The organic halide/ether ratio acts upon the activity of the catalyst component. The chlorobenzene/dibutyl ether volume ratio may for example vary between 75:25 and 35:65, preferably between 70:30 and 50:50.

Small amounts of iodine and/or alkyl halides can be added to cause the reaction between the metallic magnesium and the organic halide R$^9$X to proceed at a higher rate. Examples of alkyl halides are butyl chloride, butyl bromide and 1,2-dibromoethane. When the organic halide R$^9$X is an alkyl halide, iodine and 1,2-dibromoethane are preferably used.

The reaction temperature for preparing R$^9_z$MgX$_{2-z}$ normally is between 20 and 150° C.; the reaction time is normally between 0.5 and 20 hours. After the reaction for preparing R$^9_z$MgX$_{2-z}$ is completed, the dissolved reaction product may be separated from the solid residual products.

Step ii)

The first intermediate reaction product can be contacted in step ii) with at least one activating compound selected from the group formed by electron donors and compounds of formula M(OR$^{10}$)$_{v-w}$(OR$^{11}$)$_w$, wherein M can be Ti, Zr, Hf, Al or Si, and M(OR$^{10}$)$_{v-w}$(R$^{11}$)$_w$, wherein M is Si, each R$^{10}$ and R$^{11}$, independently, represent an alkyl, alkenyl or aryl group, v is the valency of M, being either 3 or 4, and w is smaller than v.

In an embodiment, the first intermediate reaction product can be contacted in step ii) with at least one activating compound selected from the group formed by compounds of formula $M(OR^{10})_{v-w}(R^{11})_w$, wherein M is Si, each $R^{10}$ and $R^{11}$, independently, represent an alkyl, alkenyl or aryl group, v is the valency of M, being either 3 or 4, and w is smaller than v.

The electron donor and the compounds of formula $M(OR^{10})_{v-w}(OR^{11})_w$ and $M(OR^{10})_{v-w}(R^{11})_w$ may be also referred herewith as activating compounds.

Examples of suitable electron donors that can be used in step ii) are known to the skilled person and include alcohols, carboxylic acids and carboxylic acid derivatives. Preferably, an alcohol is used as the electron donor in step ii). More preferably, the alcohol is a linear or branched aliphatic having 1-12 carbon atoms or aromatic having 6-12 carbon atoms. Even more preferably, the alcohol is selected from methanol, ethanol, butanol, isobutanol, hexanol, xylenol and benzyl alcohol. Most preferably, the alcohol is ethanol or methanol.

Examples of suitable carboxylic acids include formic acid, acetic acid, propionic acid, butyric acid, isobutanoic acid, acrylic acid, methacrylic acid, maleic acid, fumaric acid, tartaric acid, cyclohexanoic monocarboxylic acid, cis-1,2-cyclohexanoic dicarboxylic acid, phenylcarboxylic acid, toluenecarboxylic acid, naphthalene carboxylic acid, phthalic acid, isophthalic acid, terephthalic acid and/or trim-ellitic acid.

$R^{10}$ and $R^{11}$ groups can be a linear, branched or cyclic alkyl or alkenyl group, suitable groups containing from 1 to 20 carbon atoms, preferably 1-12 or 1-8 carbon atoms. In case $R^{10}$ and $R^{11}$ are cyclic groups, they may have 3-20 carbon atoms. The groups may differ independently or be the same. Preferably, at least one of the $R^{10}$ groups represents an ethyl group. In preferred embodiments, $R^{10}$ and $R^{11}$ are ethyl, propyl or butyl; more preferably, all groups are ethyl groups. $R^{10}$ and $R^{11}$ can also be aromatic hydrocarbon groups, optionally substituted with e.g. alkyl groups and can contain for example from 6 to 20 carbon atoms.

Preferably, M in said activating compound is Ti or Si. Preferably, the value of w is 0, the activating compound being for example a titanium tetraalkoxide containing 4-32 C-atoms. The four alkoxide groups in the compound may be the same or may differ independently. Preferably, at least one of the alkoxy groups in the compound is an ethoxy group. More preferably the compound is a tetraalkoxide, like titanium tetraethoxide. Si-containing compounds suitable as activating compounds are the same as listed above for step i).

Preferably, a Ti-based compound, for example titanium tetraethoxide, is used together with an alcohol, like ethanol or methanol in step ii) to give the second intermediate reaction product.

If two or more compounds are used in step ii) of the preferred process according to the invention, their order of addition is not critical, but may affect catalyst performance depending on the compounds used. A skilled person may optimize their addition based on some experiments. The compounds of step ii) can be added together or sequentially.

The first intermediate reaction product can be contacted in any sequence with at least one electron donor and/or a compound of formula $M(OR^{10})_{v-w}(OR^{11})_w$ or $M(OR^{10})_{v-w}(R^{11})_w$. Preferably, the electron donor is first added to the first intermediate reaction product and then the compound $M(OR^{10})_{v-w}(OR^{11})_w$ or $M(OR^{10})_{v-w}(R^{11})_w$ is added; in this order no agglomeration of solid particles is observed. The compounds in step ii) are preferably added slowly, for instance during a period of 0.1-6, preferably during 0.5-4 hours, most preferably during 1-2.5 hours, each.

The first intermediate reaction product and the electron donor and/or the compound of formula $M(OR^{10})_{v-w}(OR^{11})_w$ or $M(OR^{10})_{v-w}(R^{11})_w$ may be contacted with an inert dispersant in step ii). The dispersant is preferably chosen such that virtually all side products are dissolved in the dispersant and/or to act as an inert diluent for the Mg-containing support particles. Any substance known in the art that is inert to the Mg-containing support particles may be used as inert dispersant. The dispersant may be an aromatic or aliphatic hydrocarbon compound. The inert dispersant is preferably a hydrocarbon solvent and more preferably it is selected from the groups of linear and branched aliphatic and aromatic hydrocarbon compounds with, for instance, 4-20 C-atoms. Suitable dispersants include for example aliphatic and aromatic hydrocarbons and halogenated aromatic solvents with for instance 4-20 C-atoms; alkyl and aryl halides; ethers. Preferably, the dispersant is an aliphatic hydrocarbon, more preferably pentane, iso-pentane, hexane or heptane, heptane being most preferred.

In the preferred process according to the invention the molar ratio of activating compound to the magnesium atom of the first intermediate reaction product may range between wide limits and is, for instance, between 0.02 and 1.0. Preferably the molar ratio is between 0.1 and 0.7, depending on the type of activating compound. In the process according to the invention the temperature in step ii) can be in the range from −20° C. to 70° C., preferably from −10° C. to 50° C., more preferably in the range between 0° C. and 30° C. Preferably, at least one of the reaction components is dosed in time, for instance during 0.1 to 6, preferably during 0.5 to 4 hours, more particularly during 1-2.5 hours.

The obtained second intermediate reaction product may be a solid and may be further washed, preferably with the solvent also used as inert dispersant; and then stored and further used as a suspension in said inert solvent. Alternatively, the product may be dried, preferably partly dried, preferably slowly and under mild conditions; e.g. at ambient temperature and pressure.

Starting from a solid Mg-containing product of controlled morphology, said morphology is not negatively affected during treatment with the activating compound. The solid second intermediate reaction product obtained is considered to be an adduct of the Mg-containing compound and the at least one compound as defined in step ii), and is still of controlled morphology. This second intermediate reaction product being a solid catalyst support containing magnesium is subsequently contacted in step iii) with a halogen-containing titanium compound and electron donor compound.

Preferably, the solid first intermediate reaction product is contacted with an alcohol and then with a titanium tetraalkoxide and an inert dispersant to give a solid second intermediate reaction product. This second intermediate reaction product is preferably then contacted in step iii) with titanium tetrachloride, a monoester, the first internal donor represented by formula (I) and optionally a second internal electron donor selected from a group consisting of diesters and diethers.

Step iii)

The Ti/Mg molar ratio in the reaction between the second intermediate reaction product and halogen-containing titanium compound preferably is between 10 and 100, most preferably, between 10 and 50. Titanium tetrachloride is the most preferred halogen-containing titanium compound.

The second intermediate reaction product can be contacted with the halogen-containing Ti-compound, the monoester, the compound represented by formula (I) and optionally, the second internal electron donor in any order, at any time and any stage that the contacting reaction may be performed at and by applying any method known to the skilled person in the art.

For instance, the contact of the second intermediate reaction product with the halogen-containing Ti-compound in step iii) can be done once (which may be also referred to herein as stage I) and/or this contacting step can be repeated several times, preferably it can be repeated once, twice or three times. For instance, the solid intermediate reaction product may be contacted a second time (which may be also referred to herein as stage II) and/or a third time (which may be also referred to herein as stage III) with the halogen-containing Ti-compound. In between stage I, II, III and potential additional such stages, the liquid formed during said contacting reaction may be removed by using any conventional methods. The monoester, the compound of formula (I) and/or the additional internal electron donor can be added in any order and/or at any of said stages, e.g. stages I, II and III.

Preferably, the second intermediate reaction product is contacted with the halogen-containing Ti-compound and the monoester once, so at stage I.

The molar ratio of the monoester to magnesium may vary between 0.05 and 0.5; preferably between 0.2 and 0.4; and more preferably between 0.15 and 0.25.

Preferably, the compound of formula (I) may be added during the reaction of the second intermediate reaction product with the halogen-containing Ti-compound at stage I, II or III, preferably at stage II, after monoester introduction.

The molar ratio of the internal electron donor of formula (I) relative to the magnesium may vary between 0.01 and 0.2. Preferably, this molar ratio is between 0.02 and 0.15; more preferably between 0.03 and 0.1; and most preferably between 0.04 and 0.05.

Preferably, the second internal donor is added during the reaction of the second intermediate reaction product with the halogen-containing Ti-compound at stage III or in the next stage after the stage of adding the internal donor of formula (I).

The molar ratio of the second internal donor to magnesium may vary between 0.02 and 0.15; and more preferably between 0.05 and 0.1.

Preferably, during contacting the second intermediate reaction product and the halogen-containing titanium compound an inert dispersant is used. The dispersant preferably is chosen such that virtually all side products formed are dissolved in the dispersant. Suitable dispersants include for example aliphatic and aromatic hydrocarbons and halogenated aromatic solvents with for instance 4-20 C-atoms. Examples include toluene, xylene, benzene, decane, o-chlorotoluene and chlorobenzene.

The reaction temperature during contacting in step iii) the second intermediate reaction product and the halogen-containing titanium compound may be preferably between 0° C. and 150° C., more preferably between 50° C. and 150° C., and more preferably between 80° C. and 130° C., also depending of the boiling point of the components, such as the monoester used. Most preferably, the reaction temperature is between 90° C. and 120° C. The obtained reaction product may be washed, usually with an inert aliphatic or aromatic hydrocarbon or halogenated aromatic compound, to obtain the catalyst component of the invention. If desired the reaction and subsequent purification steps may be repeated one or more times. A final washing is preferably performed with an aliphatic hydrocarbon to result in a suspended or at least partly dried catalyst component, as described above for the other steps.

The invention further relates to a catalyst composition for polymerization of olefins obtainable by the process according to the invention.

The invention also relates to a polymerization catalyst system that comprises the catalyst composition according to the invention and a co-catalyst. Preferably, the catalyst system also comprises an external electron-donating compound, also referred to as external electron donor, or simply external donor. The main function of this external donor compound is to affect the stereoselectivity of the catalyst system in polymerization of olefins having 3 or more carbon atoms, and therefore it may be also referred to as selectivity control agent. Preferably, the co-catalyst is an organometallic compound containing a metal from group 1, 2, 12 or 13 of the Periodic System of the Elements (Handbook of Chemistry and Physics, 70th Edition, CRC Press, 1989-1990), wherein the system further comprises an external electron donor.

The invention further relates to a process of making a polyolefin by contacting at least one olefin with a polymerization catalyst system comprising the catalyst composition according to the present invention.

Preferably, the polyolefin made by using the catalyst system of the present invention is polypropylene. It is an advantage of the present invention that polypropylene obtainable by employing said catalyst has a broad molecular weight distribution and a low amount of atactic fraction and is obtained in high yield.

The preparation of polyolefins may take place by polymerizing one or more olefins simultaneously and/or successively in the presence of a catalyst system comprising the catalyst according to the invention, a co-catalyst and optionally an external donor. The olefin according to the invention may be selected from mono- and di-olefins containing from 2 to 10 carbon atoms, such as for example ethylene, propylene, butylene, hexene, octene and/or butadiene. According to a preferred embodiment of the invention the olefin is propylene or a mixture of propylene and ethylene, to result in a propylene homopolymer or copolymer. A propylene copolymer is herein meant to include both so-called random copolymers with relatively low comonomer content, e.g. up to 10 mol %, as well as so-called impact copolymers comprising higher comonomer contents, e.g. from 5 to 80 mol %, more typically from 10 to 60 mol %. The impact copolymers are actually blends of different propylene polymers; such copolymers can be made in one or two reactors and can be blends of a first component of low comonomer content and high crystallinity, and a second component of high comonomer content having low crystallinity or even rubbery properties. Such random and impact copolymers are well-known to the skilled in the art.

Generally, the co-catalyst is an organometallic compound containing a metal from group 1, 2, 12 or 13 of the Periodic System of the Elements (Handbook of Chemistry and Physics, 70th Edition, CRC Press, 1989-1990). Preferably, the co-catalyst is an organoaluminium compound. The organoaluminium compound may be, for instance, a compound having the formula $AlR^{15}_3$, wherein each $R^{15}$ independently represents an alkyl group with, for instance, 1-10 C-atoms or an aryl group with, for instance, 6-20 C-atoms. Examples of a suitable organoaluminium compound are trimethylaluminium, triethylaluminium, triisobutylaluminium, and/or trioctylaluminium. Preferably, the co-catalyst is triethylaluminium.

Examples of suitable external donors include organosilicon compounds. Mixtures of external donors can also be used. Examples of organo-silicon compounds that are suitable as external donor are compounds or mixtures of compounds of general formula Si(OR$^{16}$)$_{4-n}$R$^{17}$$_n$, wherein n can be from 0 up to 2 preferably n is 1 or 2 as higher values have no positive effect on stereospecificity, and each R$^{16}$ and R$^{17}$, independently, represents an alkyl or aryl group, optionally containing one or more hetero atoms for instance O, N, S or P, with, for instance, 1-20 C-atoms, as defined above for R$^{13}$ and R$^{14}$. Examples of suitable compounds include the silane-compounds that can be used at step i), as described above. Preferably the organo-silicon compound used as external donor is n-propyl trimethoxysilane. The molar ratio of the metal of the co-catalyst relative to titanium in the polymerization catalyst system during the polymerization may vary for instance from 5 to 2000. Preferably this ratio is between 50 and 300.

The aluminium/external donor molar ratio in the polymerization catalyst system preferably is between 1 (if less than 1 no polymerization occurs) and 200; more preferably between 5 and 100.

Preferably, no external donor is used in said catalyst system as higher molecular weight distribution and higher polymer yield are obtained.

The polymerization process can be carried out in the gas phase or in the liquid phase (in bulk or slurry). In the case of polymerization in a slurry (liquid phase) a dispersing agent is present. Suitable dispersing agents include for example n-butane, isobutane, n-pentane, isopentane, hexane, heptane, octane, cyclohexane, benzene, toluene, xylene and liquid propylene. The polymerization conditions of the process according to the invention, such as for example the polymerization temperature and time, monomer pressure, avoidance of contamination of catalyst, choice of polymerization medium in slurry processes, the use of further ingredients (like hydrogen) to control polymer molar mass, and other conditions are well known to persons of skill in the art. The polymerization temperature may vary within wide limits and is, for example for propylene polymerization, between 0° C. and 120° C., preferably between 40° C. and 100° C. The pressure during (propylene) (co)polymerization is for instance between 0.1 and 6 MPa, preferably between 0.5-3 MPa.

The molar mass of the polyolefin obtained during the polymerization can be controlled by adding during the polymerization hydrogen or any other agent known to be suitable for the purpose. The polymerization can be carried out in a continuous mode or batch-wise. Slurry-, bulk-, and gas-phase polymerization processes, multistage processes of each of these types of polymerization processes, or combinations of the different types of polymerization processes in a multistage process are contemplated herein. Preferably the polymerization process is a single stage gas phase process or a multistage, for instance a 2-stage, gas phase process wherein in each stage a gas-phase process is used.

Examples of gas-phase polymerization processes include both stirred bed reactors and fluidized bed reactor systems; such processes are well known in the art. Typical gas phase α-olefin polymerization reactor systems comprise a reactor vessel to which alpha-olefin monomer(s) and a catalyst system can be added and which contain an agitated bed of growing polymer particles.

The present invention further relates to the use a monoester, the compound (I) as a first internal electron donor and optionally a second internal electron donor selected from a group consisting of diesters and diethers in a catalyst composition for polymerization of olefins. Polyolefins with improved properties, such as having broad molecular weight distribution, high isotacticity and high yield are produced with said catalyst composition.

It is noted that the invention relates to all possible combinations of features recited in the claims. Features described in the description may further be combined.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention will be further elucidated with the following examples without being limited hereto.

EXAMPLES

Preparation of 4-[benzoyl(methyl)amino]pentan-2-yl benzoate (AB)

Step a)

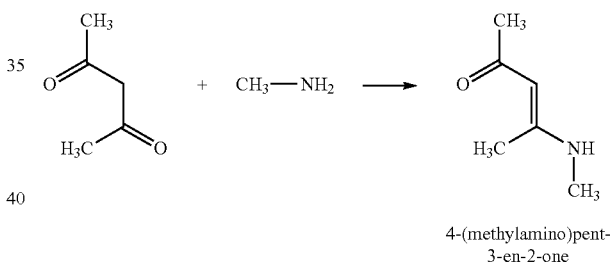

4-(methylamino)pent-3-en-2-one

40% monomethylamine solution in water (48.5 g, 0.625 mol) was added drop wise to a stirred solution of substituted pentane-2,4-dione (50 g, 0.5 mol) in toluene (150 ml. After the addition, the reaction mass was stirred at room temperature for 3 hours and then refluxed. During the reflux the water formed was azeotropically removed using a Dean-stark trap. Then the solvent was removed under reduced pressure to give 4-(methylamino)pent-3-en-2-one, 53.5 g (95% yield), which was then directly used for reduction.

Step b)

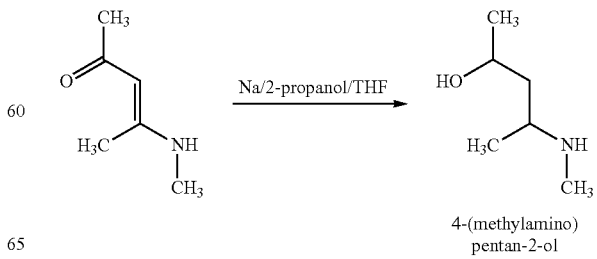

4-(methylamino)pentan-2-ol 4-(methylamino)-pent-3-en-2-one (100 g) was added to a stirred mixture of 1000 ml 2-propanol and 300 ml toluene. To this solution, small piece of metallic sodium 132 g was gradually added at a temperature of between 25-60° C. The reaction mass was refluxed for 18 h. The mass was cooled to room temperature and was poured in cold water and extracted with dichloromethane. The extract was dried over sodium sulfate, filtered and then evaporated under reduced pressure to give 65 g 4-(methylamino)pentan-2-ol (isomer mixture)oil (63% yield).

Step c)

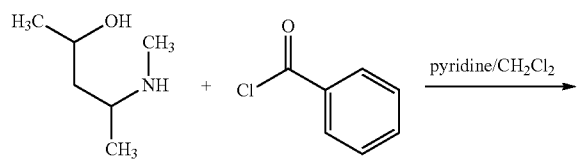

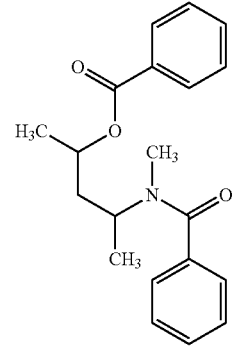

4-[benzoyl(methyl)amino]pentan-2-yl benzoate 4-(methylamino)pentan-2-ol (10 g) was added to a mixture of pyridine (16.8 g) and toluene (100 ml). The mass was cooled to 10° C. and benzoyl chloride (24 g) was added drop wise. The mixture was refluxed for 6 h. The mixture was then diluted with toluene and water. The organic layer was washed with dilutedHCl, water saturated bicarbonate and brine solution. The organic layer was dried over sodium sulfate, filtered and then evaporated under reduced pressure. The residue was purified by flash chromatography to form 25 g product as thick oil (90% yield). The product was characterized by $^1$H NMR and $^{13}$C NMR: m/z=326.4 (m+1), $^1$H NMR (300 MHz, CDCl$_3$) δ=7.95-7.91 (m, 1H), 7.66-7.60 (m, 2H), 7.40-7.03 (m, 5H), 6.78-6.76 (m, 2H), 4.74-5.06 (br m, 1H), 3.91-3.82 (m, 1H), 2.83-2.56 (ddd, 3H), 2.02-1.51 (m, 1H), 1.34-1.25 (dd, 1H), 1.13-1.02 (m, 6H); $^{13}$C NMR (75 MHz, CDCl$_3$), δ=170.9, 170.4, 170.3, 164.9, 164.6, 135.9, 135.8, 135.2, 131.8, 131.7, 131.6, 129.6, 129.4, 129.3, 128.9, 128.4, 128.3, 128.2, 128.0, 127.7, 127.3, 127.2, 127.1, 127.0, 125.7, 125.6, 125.0, 124.9, 68.3, 67.5, 67.3, 49.8, 49.4, 44.9, 44.4, 39.7, 39.0, 38.4, 38.3, 30.5, 29.8, 25.5, 25.1, 19.33, 19.1, 18.9, 18.3, 17.0, 16.8, 16.7.

By applying the same method of preparation, internal electron donors as described and characterized in Table 1 were also obtained:

TABLE 1

| Compound | Structure |
|---|---|
| 4-[benzoyl(propan-2-yl)amino]pentan-2-yl benzoate (AB-iPr): m/z = 354.5 (m + 1), $^1$H NMR (300 MHz, CDCl$_3$) δ = 8.06 (s, 2H), 7.68-7.53 (s, 1H), 7.44-7.27 (m, 7H), 5.29 (br s, 1H), 5.03 (br s, 1H), 3.91 (br s, 1H), 3.41 (br s, 1H), 2.89 (br s, 1H), 2.10-2.02 (t, 1H), 1.78-1.06 (m, 13H), $^{13}$C NMR (75 MHz, CDCl$_3$), δ = 171.6, 166.5, 138.9, 133.3, 133.2, 130.8, 129.8, 129.8, 129.0, 128.8, 128.7, 125.9, 51.4, 46.9, 42.3, 41.1, 21.3, 21.1, 18.2. | C$_6$H$_5$ ... C$_6$H$_5$ |

Example 1

A. Grignard Formation Step

This step was carried out as described in Example XVI of EP 1 222 214 B1.

A stainless steel reactor of 9 l volume was filled with magnesium powder 360 g. The reactor was brought under nitrogen. The magnesium was heated at 80° C. for 1 hour, after which a mixture of dibutyl ether (1 liter) and chlorobenzene (200 ml) was added. Then iodine (0.5 g) and n-chlorobutane (50 ml) were successively added to the reaction mixture. After the colour of the iodine had disappeared, the temperature was raised to 94° C. Then a mixture of dibutyl ether (1.6 liter) and chlorobenzene (400 ml) was slowly added for 1 hour, and then 4 liter of chlorobenzene was slowly added for 2.0 hours. The temperature of reaction mixture was kept in interval 98-105° C. The reaction mixture was stirred for another 6 hours at 97-102° C. Then the stirring and heating were stopped and the solid material was allowed to settle for 48 hours. By decanting the solution above the precipitate, a solution of phenylmagnesiumchloride reaction product A has been obtained with a concentration of 1.3 mol Mg/l. This solution was used in the further catalyst preparation.

B. Preparation of the First Intermediate Reaction Product

This step was carried out as described in Example XX of EP 1 222 214 B1, except that the dosing temperature of the reactor was 35° C., the dosing time was 360 min and the propeller stirrer was used. 250 ml of dibutyl ether was introduced to a 1 liter reactor. The reactor was fitted by propeller stirrer and two baffles. The reactor was thermostated at 35° C.

The solution of reaction product of step A (360 ml, 0.468 mol Mg) and 180 ml of a solution of tetraethoxysilane (TES) in dibutyl ether (DBE), (55 ml of TES and 125 ml of DBE), were cooled to 10° C., and then were dosed simultaneously to a mixing device of 0.45 ml volume supplied with a stirrer and jacket. Dosing time was 360 min. Thereafter the premixed reaction product A and the TES-solution were introduced to a reactor. The mixing device (minimixer) was cooled to 10° C. by means of cold water circulating in the minimixer's jacket. The stirring speed in the minimixer was 1000 rpm. The stirring speed in reactor was 350 rpm at the beginning of dosing and was gradually increased up to 600 rpm at the end of dosing stage.

On the dosing completion the reaction mixture was heated up to 60° C. and kept at this temperature for 1 hour. Then the stirring was stopped and the solid substance was allowed to settle. The supernatant was removed by decanting. The solid substance was washed three times using 500 ml of heptane. As a result, a pale yellow solid substance, reaction product B (the solid first intermediate reaction product; the support), was obtained, suspended in 200 ml of heptane. The average particle size of support was 22 μm and span value $(d_{90}-d_{10})/d_{50}=0.5$.

C. Preparation of the Second Intermediate Reaction Product

Support activation was carried out as described in Example IV of WO/2007/134851 to obtain the second intermediate reaction product.

In inert nitrogen atmosphere at 20° C. a 250 ml glass flask equipped with a mechanical agitator is filled with slurry of 5 g of reaction product B dispersed in 60 ml of heptane. Subsequently a solution of 0.22 ml ethanol (EtOH/Mg=0.1) in 20 ml heptane is dosed under stirring during 1 hour. After keeping the reaction mixture at 20° C. for 30 minutes, a solution of 0.79 ml titanium tetraethoxide (TET/Mg=0.1) in 20 ml of heptane was added for 1 hour.

The slurry was slowly allowed to warm up to 30° C. for 90 min and kept at that temperature for another 2 hours. Finally the supernatant liquid is decanted from the solid reaction product (the second intermediate reaction product; activated support) which was washed once with 90 ml of heptane at 30° C.

D. Preparation of the Catalyst Component

A reactor was brought under nitrogen and 125 ml of titanium tetrachloride was added to it. The reactor was heated to 90° C. and a suspension, containing about 5.5 g of activated support in 15 ml of heptane, was added to it under stirring. The reaction mixture was kept at 90° C. for 10 min. Then add 0.866 g of ethyl acetate (EA/Mg=0.25 mol). The reaction mixture was kept for 60 min (stage I of catalyst preparation). Then the stirring was stopped and the solid substance was allowed to settle. The supernatant was removed by decanting, after which the solid product was washed with chlorobenzene (125 ml) at 100° C. for 20 min. Then the washing solution was removed by decanting, after which a mixture of titanium tetrachloride (62.5 ml) and chlorobenzene (62.5 ml) was added. The temperature of reaction mixture was increased to 115° C. and 0.64 g of 4-[benzoyl(methyl)amino]pentan-2-yl benzoate (aminobenzoate, AB, AB/Mg=0.05 mol) in 2 ml of chlorobenzene was added to reactor. Then the reaction mixture was kept at 115° C. for 30 min (stage II of catalyst preparation). After which the stirring was stopped and the solid substance was allowed to settle. The supernatant was removed by decanting, after which a mixture of titanium tetrachloride (62.5 ml) and chlorobenzene (62.5 ml) was added. The reaction mixture was kept at 115° C. for 30 min (stage Ill of catalyst preparation), after which the solid substance was allowed to settle. The supernatant was removed by decanting and the solid was washed five times using 150 ml of heptane at 60° C., after which the catalyst component, suspended in heptane, was obtained.

E. Polymerization of Propylene

Polymerization of propylene was carried out in a stainless steel reactor (with a volume of 0.7 l) in heptane (300 ml) at a temperature of 70° C., total pressure 0.7 MPa and hydrogen presence (55 ml) for 1 hour in the presence of a catalyst system comprising the catalyst component according to step D, triethylaluminium and n-propyltrimethoxysilane. The concentration of the catalyst component was 0.033 g/l; the concentration of triethylaluminium was 4.0 mmol/l; the concentration of n-propyltrimethoxysilane was 0.2 mmol/l.

Data on the catalyst performance at the propylene polymerization are presented in Table 2. In all Tables herein, monoester (ME) refers to EA, EB or AA.

Example 1a

Example 1a was carried out in the same way as Example 1, but in step E no n-propyltrimethoxysilane was used.

Example 2

Example 2 was carried out in the same way as Example 1, but AB/Mg=0.04 in step D was used instead of AB/Mg=0.05.

Example 3

Example 3 was carried out in the same way as Example 2, but 1.27 g of amyl acetate (AA/Mg=0.25) in step D was used instead of ethyl acetate (EA/Mg=0.25).

Example 4

Example 4 was carried out in the same way as Example 1, but in step D 0.886 g of ethyl benzoate (EB/Mg=0.15) at 100° C. and AB/Mg=0.15 were used instead of EA/Mg=0.25 at 90° C. and AB/Mg=0.05, respectively.

Example 5

Example 5 was carried out in the same way as Example 4, but AB/Mg=0.05 in step D was used instead of AB/Mg=0.15.

Example 5a

Example 5a was carried out in the same way as Example 5, but in step E no n-propyltrimethoxysilane was used.

Example 6

Example 6 was carried out in the same way as Example 4, but AB/Mg=0.04 in step D was used instead of AB/Mg=0.15.

Comparative Example A (CE-A)

CE-A was carried out in the same way as Example 1, but 0.61 g of 4-(phenylcarbonyl)amino]pentan-2-yl benzoate (AB-H: N—H group is present in AB instead of N-Me group) at AB-H/Mg=0.05 in step D was used instead of AB/Mg=0.05.

Comparative Example B (CE-B)

CE-B was carried out in the same way as CE-A, but in step E no n-propyltrimethoxysilane was used.

Comparative Example C (CE-C)

CE-C was carried out in the same way as Example 1, but no AB was added in step D.

Comparative Example D (CE-D)

CE D was carried out in the same way as Example 5, but AB-H/Mg=0.05 in step D was used instead of AB/Mg=0.05.

Comparative Example E (CE-E)

CE-E was carried out in the same way as CE-D, but in step E no n-propyltrimethoxysilane was used.

Comparative Example F (CE-F)

CE-F was carried out in the same way as Example 4, but no AB was added in step D.

Comparative Example G (CE-G)

CE-G was carried out in the same way as Example 1, but the preparation of the catalyst component in step D was performed as follows.

A reactor was brought under nitrogen and 125 ml of titanium tetrachloride was added to it. The reactor was heated to 100° C. and a suspension, containing about 5.5 g of activated support in 15 ml of heptane, was added to it under stirring. Then the temperature of reaction mixture was increased to 110° C. for 10 min and 1.92 g of 4-[benzoyl (methyl)amino]pentan-2-yl benzoate (aminobenzoate, AB, AB/Mg=0.15) in 3 ml of chlorobenzene was added to reactor. Then the reaction mixture was kept at 115° C. for 105 min (stage I of catalyst preparation). Then the stirring was stopped and the solid substance was allowed to settle. The supernatant was removed by decanting, after which the solid product was washed with chlorobenzene (125 ml) at 100° C. for 20 min. Then the washing solution was removed by decanting, after which a mixture of titanium tetrachloride (62.5 ml) and chlorobenzene (62.5 ml) was added. The reaction mixture was kept at 115° C. for 30 min (stage II of catalyst preparation), after which the solid substance was allowed to settle. The supernatant was removed by decanting, and the last treatment was repeated once again (stage III of catalyst preparation). The solid substance obtained was washed five times using 150 ml of heptane at 60° C., after which the catalyst component, suspended in heptane, was obtained.

Comparative Example H (CE-H)

CE-H was carried out in the same way as CE-G, but in step E no n-propyltrimethoxysilane was used.

Data on the catalyst performance at the propylene polymerization (Examples 1-8 and CE-A to CE-H) are presented in Table 2.

Example 7

Example 7 was carried out in the same way as step D in Example 1, but 5 g of Mg(OEt)$_2$ (Aldrich grade) as the Mg-containing support, 0.97 g of ethyl acetate (EA/Mg=0.25 mol) and 0.72 g of AB (AB/Mg=0.05) were used instead of 5.5 g of activated support, 0.866 g of ethyl acetate and 0.64 g of AB.

Data on the catalyst performance at the propylene polymerization are presented in Table 4.

Comparative Example I (CE-I)

CE-I was carried out in the same way as step D in CE-G, but 5 g of Mg(OEt)$_2$ (Aldrich grade) as the Mg-containing support and 2.15 g of AB (AB/Mg=0.15) were used instead of 5.5 g of activated support and 1.92 g of AB.

Example 8

Example 8 was carried out in the same way as step D in Example 1, but 5 g of the Mg-containing support prepared according to U.S. Pat. No. 5,077,357, 0.64 g of ethyl acetate (EA/Mg=0.25 mol) and 0.48 g of AB (AB/Mg=0.05) were used instead of 5.5 g of activated support, 0.866 g of ethyl acetate and 0.64 g of AB.

Comparative Example J (CE-J)

CE-J was carried out in the same way as step D in CE-G, but 5 g of the Mg-containing support prepared according to U.S. Pat. No. 5,077,357 and 1.43 g of AB (AB/Mg=0.15) were used instead of 5.5 g of activated support and 1.92 g of AB.

Data on the catalyst performance at the propylene polymerization (Examples 7-8 and CE-I and CE-J) are presented in Table 3.

Example 9

Example 9 was carried out in the same way as Example 5, but III stage of catalyst preparation in step D was performed in the presence of 0.54 g of di-n-butylphthalate (DBP/Mg=0.05) as the another internal donor ID$_2$. After the removal of the supernatant III stage without any donor was repeated once again (as IV stage of catalyst preparation).

Example 9a

Example 9a was carried out in the same way as Example 9, but in step E no n-propyltrimethoxysilane was used.

Example 10

Example 10 was carried out in the same way as Example 9, but AB/Mg=0.018 and DBP/Mg=0.1 in step D was used instead of AB/Mg=0.05 and DBP/Mg=0.05.

Example 11

Example 11 was carried out in the same way as Example 9, but 0.5 g of 9,9-bis-methoxymethyl-fluorene (flu) (flu/Mg=0.05) in step D was used instead of 0.54 g of di-n-butylphthalate (DBP/Mg=0.05).

Example 11a

Example 11a was carried out in the same way as Example 11, but in step E no n-propyltrimethoxysilane was used.

Example 12

Example 12 was carried out in the same way as Example 11, but AB/Mg=0.025 in step D was used instead of AB/Mg=0.05.

Example 12a

Example 12a was carried out in the same way as Example 11, but in step E no n-propyltrimethoxysilane was used.

Data on the catalyst performance at the propylene polymerization (Examples 9-12) are presented in Table 4.

TABLE 2

| Ex. No. | ID$_1$/Mg | ME/Mg | ID$_1$, wt. % | Ti, wt. % | PP yield, kg/g cat. | APP, wt. % | XS, % | MFR, dg/min | Mw/Mn |
|---|---|---|---|---|---|---|---|---|---|
| 1 | 0.05 (AB) | 0.25 (EA) | 12.7 | 4.4 | 9.2 | 0.84 | 4.5 | 0.7 | 7.6 |
| 1a | 0.05 (AB) | 0.25 (EA) | 12.7 | 4.4 | 11.4 | 1.9 | 5.2 | 2.2 | 8.3 |
| 2 | 0.04 (AB) | 0.25 (EA) | 10.2 | 4.1 | 13.1 | 1.2 | 6.8 | 3.0 | 7.1 |
| 3 | 0.04 (AB) | 0.25 (AA) | 10.1 | 3.6 | 8.4 | 1.4 | 3.7 | 1.3 | 8.1 |
| 4 | 0.15 (AB) | 0.15 (EB) | 11.4 | 3.0 | 9.7 | 0.6 | 3.2 | 1.8 | 8.7 |
| 5 | 0.05 (AB) | 0.15 (EB) | 11.8 | 3.5 | 10.0 | 0.95 | 3.5 | 1.4 | 7.0 |
| 5a | 0.05 (AB) | 0.15 (EB) | 11.8 | 3.5 | 10.2 | 2.6 | 5.0 | 2.6 | 8.2 |
| 6 | 0.04 (AB) | 0.15 (EB) | 11.6 | 3.5 | 11.3 | 1.4 | 3.3 | 1.8 | 7.1 |
| CE-A | 0.05 (AB-H) | 0.25 (EA) | 8.5 | 3.3 | 9.2 | 1.6 | 4.2 | 5.9 | 6.2 |
| CE-B | 0.05 (AB-H) | 0.25 (EA) | 8.5 | 3.3 | 12.6 | 5.5 | 12.5 | 13.0 | 6.4 |
| CE-C | 0 | 0.25 (EA) | 0 | 3.8 | 5.3 | 7.3 | 10.8 | 19.2 | 5.1 |
| CE-D | 0.05 (AB-H) | 0.15 (EB) | 7.0 | 3.2 | 9.1 | 1.7 | 6.5 | 7.4 | 5.3 |
| CE-E | 0.05 (AB-H) | 0.15 (EB) | 7.0 | 3.2 | 14.6 | 13.0 | 16.7 | 22.8 | 5.6 |
| CE-F | 0 | 0.15 (EB) | 0 | 2.6 | 5.3 | 7.1 | 12.0 | 22.6 | 5.8 |
| CE-G | 0.15 (AB) | 0 | 17.9 | 3.2 | 4.4 | 1.1 | 2.5 | 0.6 | 7.7 |
| CE-H | 0.15 (AB) | 0 | 17.9 | 3.2 | 5.3 | 1.5 | 4.5 | 0.9 | 8.2 |

TABLE 3

| Ex. No. | Support | ID$_1$/Mg | ME/Mg | ID$_1$, wt. % | Ti, wt. % | PP yield, kg/g cat. | APP, wt. % | XS, % | MFR, dg/min | Mw/Mn |
|---|---|---|---|---|---|---|---|---|---|---|
| 7 | Mg(OEt)$_2$ | 0.05 (AB) | 0.25 (EA) | 11.7 | 4.0 | 15.5 | 0.8 | 2.7 | 2.2 | 7.3 |
| CE-I | Mg(OEt)$_2$ | 0.15 (AB) | 0 | 19.8 | 4.5 | 5.5 | 1.4 | 2.7 | 0.9 | 7.8 |
| 8 | * | 0.05 (AB) | 0.25 (EA) | 13.2 | 4.6 | 13.5 | 0.7 | 2.6 | 2.3 | 7.9 |
| CE-J | * | 0.15 (AB) | 0 | 20.4 | 4.3 | 6.3 | 0.9 | 2.5 | 1.1 | 7.5 |

* = catalyst support prepared according to the procedure described in U.S. Pat. No. 5,077,357

TABLE 4

| Ex. No. | ID$_1$/Mg | ID$_2$/Mg | ME/Mg | ID$_1$, wt. % | ID$_2$, wt. % | Ti, wt. % | PP yield, kg/g cat. | APP wt. % | XS, % | MFR, dg/min | Mw/Mn |
|---|---|---|---|---|---|---|---|---|---|---|---|
| 9 | 0.05 (AB) | 0.05 (DBP) | 0.15 (EB) | 11.3 | 6.4 | 3.2 | 9.8 | 0.8 | 4.1 | 2.7 | 8.4 |
| 9a | 0.05 (AB) | 0.05 (DBP) | 0.15 (EB) | 11.3 | 6.4 | 3.2 | 10.9 | 3.0 | 7.5 | 3.5 | 8.9 |
| 10 | 0.018 (AB) | 0.1 (DBP) | 0.15 (EB) | 5.1 | 9.5 | 2.5 | 10.0 | 0.5 | 3.2 | 8.3 | 6.8 |
| 11 | 0.05 (AB) | 0.05 (flu) | 0.15 (EB) | 10.6 | 7.6 | 2.7 | 11.1 | 0.5 | 2.0 | 2.2 | 7.2 |
| 11a | 0.05 (AB) | 0.05 (flu) | 0.15 (EB) | 10.6 | 7.6 | 2.7 | 12.3 | 0.6 | 2.5 | 4.1 | 7.2 |
| 12 | 0.025 (AB) | 0.05, (flu) | 0.15 (EB) | 6.3 | 8.6 | 2.4 | 9.8 | 0.5 | 2.2 | 3.3 | 6.5 |
| 12a | 0.025 (AB) | 0.05, (flu) | 0.15 (EB) | 6.3 | 8.6 | 2.4 | 10.0 | 0.6 | 3.1 | 5.0 | 6.9 |

Abbreviations and measuring methods:

PP yield, kg/g cat is the amount of polypropylene obtained per gram of catalyst component.

APP, wt % is the weight percentage of atactic polypropylene. Atactic PP is the PP fraction soluble in heptane during polymerization. APP was determined as follows: 100 ml of the filtrate (y ml) obtained in separating the polypropylene powder (x g) and the heptane was dried over a steam bath and then under vacuum at 60° C. That yielded z g of atactic PP. The total amount of Atactic PP (q g) is: (y/100)*z. The weight percentage of Atactic PP is: (q/(q+x))*100%.

XS, wt % is xylene solubles, measured according to ASTM D 5492-10.

MFR is the melt flow rate as measured at 230° C. with 2.16 kg load, measured according to ISO 1133.

Mw/Mn: Polymer molecular weight and its distribution (MWD) were determined by Waters 150° C. gel permeation chromatograph combined with a Viscotek 100 differential viscosimeter. The chromatograms were run at 140° C. using 1,2,4-trichlorobenzene as a solvent with a flow rate of 1 ml/min. The refractive index detector was used to collect the signal for molecular weights.

The $^1$H-NMR and $^{13}$C-NMR spectra were recorded on a Varian Mercury-300 MHz NMR Spectrometer, using deuterated chloroform as a solvent.

In addition to the broader molecular weight distribution and high isotacticity shown, the catalysts prepared with monoester and AB as the internal donor show significantly (2-3 times) higher activity compared to the catalyst prepared with AB without monoester. In addition, using monoester significantly lowers (3 times) amount of AB required for preparing the catalysts.

Polymerizations without an external donor compared to ones with n-propyltrimethoxysilane as external donor show that the polymer yield increases; the hydrogen sensitivity (MFR values) increases; MWD of polymers (Mw/Mn values) are similar or slightly broader; and the stereospecificity of the AB-containing catalysts is good (APP and XS values are similar or increase insignificantly).

The addition of diester (DBP) as the second internal donor in catalyst composition allows increasing the hydrogen sensitivity (MFR values) at broad MWD (Ex. 9 and Ex. 10) and increasing the sensitivity to external donor (compare APP and XS values in Ex. 9 and Ex. 9a). The addition of 1,3-diether (flu) as the second internal donor in catalyst composition allows increasing the hydrogen and obtaining polymers with increased isotacticity (minimum XS values) can be produced (Ex. 11-12).

By using a known internal electron donor (AB-H), Mw/Mn values are lower, the atactic fraction is higher and/or the polymer yields are lower in the polymers obtained then for the internal donor according to the present invention.

The invention claimed is:

1. A catalyst composition for polymerization of olefins comprising a monoester and an internal electron donor represented by formula (I),

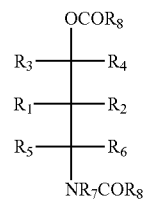

Formula (I)

wherein:

$R_1$, $R_2$, $R_3$, $R_4$, $R_5$ and $R_6$ are the same or different and are independently selected from the group consisting of hydrogen, straight, branched and cyclic alkyl having at most 20 carbon atoms and aromatic substituted and unsubstituted hydrocarbyl having 6 to 20 carbon atoms;

$R_7$ is selected from the group consisting of straight, branched and cyclic alkyl having at most 20 carbon atoms and aromatic substituted and unsubstituted hydrocarbyl having 6 to 20 carbon atoms; and $R_8$ is selected from the group consisting of aromatic substituted and unsubstituted hydrocarbyl having 6 to 20 carbon atoms.

2. The catalyst composition according to claim 1, wherein $R_1$, $R_2$, $R_3$, $R_4$, $R_5$ and $R_6$ are independently selected from the group consisting of hydrogen, methyl, ethyl, propyl, isopropyl, butyl, tert-butyl, phenyl, trifluoromethyl and halophenyl.

3. The catalyst composition according claim 1, wherein when one of $R_3$ and $R_4$ has at least one carbon atom then the other one of $R_3$ and $R_4$ is hydrogen and wherein when one of $R_5$ and $R_6$ has at least one carbon atom then the other one of $R_5$ and $R_6$ is a hydrogen atom.

4. The catalyst composition according to claim 1, wherein $R_7$ is selected from a group consisting of methyl, ethyl, propyl, isopropyl, butyl, tert-butyl, phenyl, benzyl, substituted benzyl and halophenyl and/or wherein $R_8$ is substituted or unsubstituted phenyl, benzyl, naphthyl, ortho-tolyl, para-tolyl or anisol.

5. The catalyst composition according to claim 1, wherein the monoester is an acetate or a benzoate.

6. The catalyst composition according to claim 1, comprising a magnesium-containing support, a halogen-containing titanium compound, said monoester and said internal electron donor according to formula (I).

7. The catalyst composition according to claim 1, further comprising a second additional internal electron donor, wherein the second electron donor is selected from the group consisting of diesters and diethers.

8. The catalyst composition according to claim 6, further comprising the second internal electron donor, wherein the second internal electron donor is selected from the group consisting of diesters and diethers, wherein the molar ratio of the additional internal electron donor to magnesium of said magnesium-containing support is between 0.02 and 0.15.

9. A process for preparing a catalyst composition, comprising contacting a magnesium-containing support with a halogen-containing titanium compound, a monoester, a first internal electron donor represented by formula (I), and optionally a second internal electron donor selected from a group consisting of diesters and diethers,

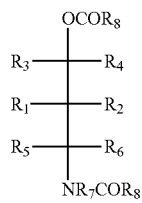

Formula (I)

wherein:
R$_1$, R$_2$, R$_3$, R$_4$, R$_5$ and R$_6$ are the same or different and are independently selected from the group consisting of hydrogen, straight, branched and cyclic alkyl having at most 20 carbon atoms and aromatic substituted and unsubstituted hydrocarbyl having 6 to 20 carbon atoms;
R$_7$ is selected from the group consisting of straight, branched and cyclic alkyl having at most 20 carbon atoms and aromatic substituted and unsubstituted hydrocarbyl having 6 to 20 carbon atoms; and
R$_8$ is selected from the group consisting of aromatic substituted and unsubstituted hydrocarbyl having 6 to 20 carbon atoms.

10. The process according to claim 9, which comprises:
i) contacting a compound R$^9_z$MgX$_{2-z}$ wherein R$^9$ is aromatic, aliphatic or cyclo-aliphatic group containing 1 to 20 carbon atoms, X is a halide, and z is in a range of larger than 0 and smaller than 2, with an alkoxy- or aryloxy-containing silane compound to give a first intermediate reaction product;
ii) contacting the first intermediate reaction product with at least one activating compound selected from the group of electron donors and compounds of formula M(OR$^{10}$)$_{v-w}$(OR$^{11}$)$_w$ wherein M is Ti, Zr, Hf, Al or Si, or M(OR$^{10}$)$_{v-w}$(R$^{11}$)$_w$ wherein M is Si, each R$^{10}$ and R$^{11}$, independently, represent an alkyl, alkenyl or aryl group, v is the valency of M, v being either 3 or 4, and w is smaller than v to give a second intermediate reaction product; and
iii) contacting the second intermediate reaction product with a halogen-containing Ti-compound, the monoester, the compound represented by formula (I) as the first internal electron donor, and optionally the diester or diether as the second internal electron donor.

11. A catalyst composition manufactured by the process according to claim 9.

12. A polymerization catalyst system comprising the catalyst composition according to claim 1, a co-catalyst and optionally an external electron donor.

13. A process of making a polyolefin comprising contacting an olefin with the catalyst system according to claim 12.

14. A catalyst composition for the polymerization of olefins, comprising
an acetate or benzoate monoester;
a compound represented by formula (I) as a first internal electron donor

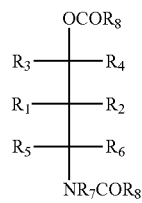

Formula (I)

wherein:
R$_1$, R$_2$, R$_3$, R$_4$, R$_5$ and R$_6$ are the same or different and are independently selected from the group consisting of hydrogen, methyl, ethyl, propyl, isopropyl, butyl, tert-butyl, phenyl, trifluoromethyl and halophenyl,
R$_7$ is selected from the group consisting of methyl, ethyl, propyl, isopropyl, butyl, tert-butyl, phenyl, benzyl, substituted benzyl and halophenyl, and
R$_8$ is selected from the group consisting of substituted or unsubstituted phenyl, benzyl, naphthyl, ortho-tolyl, para-tolyl or anisol;
a magnesium-containing support;
a halogen-containing titanium compound; and
optionally a second internal electron donor selected from a group consisting of diesters and diethers.

15. The catalyst composition of claim 14, wherein
the monoester is ethyl acetate, amyl acetate or ethyl benzoate;
R$_1$ and R$_2$ are each a hydrogen atom; and
when one of R$_3$ and R$_4$ has at least one carbon atom then the other one of R$_3$ and R$_4$ is hydrogen and wherein when R$_5$ and R$_6$ has at least one carbon atom then the other one of R$_5$ and R$_6$ is a hydrogen atom.

16. A process for the manufacture of the catalyst composition of claim 14, which comprises:
i) contacting a compound R$^9_z$MgX$_{2-z}$ wherein R$^9$ is aromatic, aliphatic or cyclo-aliphatic group containing 1 to 20 carbon atoms, X is a halide, and z is in a range of larger than 0 and smaller than 2, with an alkoxy- or aryloxy-containing silane compound to give a first intermediate reaction product;
ii) contacting the first intermediate reaction product with at least one activating compound selected from the group of electron donors and a compound of the formula M(OR$^{10}$)$_{v-w}$(R$^{11}$)$_w$ wherein M is Si, each R$^{10}$ and R$^{11}$, independently, represent an alkyl, alkenyl or aryl group, v is the valency of M, v being either 3 or 4, and w is smaller than v to give a second intermediate reaction product; and
iii) contacting the second intermediate reaction product with a halogen-containing Ti-compound, the monoester, the compound represented by formula (I) as the first internal electron donor, and optionally the second internal electron donor.

17. A polymerization catalyst system comprising the catalyst composition according to claim 14, a co-catalyst, and optionally an external electron donor.

18. A process of making a polyolefin comprising contacting an olefin with the catalyst system according to claim 17.

* * * * *